United States Patent [19]

Taenzer

[11] 4,238,962
[45] Dec. 16, 1980

[54] TRANSDUCER DRIVE FOR ULTRASONIC IMAGING

[75] Inventor: Jon C. Taenzer, Palo Alto, Calif.

[73] Assignee: Picker Corporation, Northford, Conn.

[21] Appl. No.: 938,073

[22] Filed: Aug. 30, 1978

[51] Int. Cl.³ ............................................. G01N 29/00
[52] U.S. Cl. ........................................ 73/633; 74/108
[58] Field of Search ............... 73/633, 635, 644, 618, 73/620, 629; 128/660; 340/3 R, 5 R, 5 MP; 74/108, 105, 102; 367/7, 103, 119, 120

[56] References Cited

U.S. PATENT DOCUMENTS

| | | | |
|---|---|---|---|
| 2,706,913 | 4/1955 | Trossi | 74/108 |
| 2,972,264 | 2/1961 | Birkbeck et al. | 74/108 |
| 3,857,052 | 12/1974 | Beller | 73/620 |
| 3,886,490 | 5/1975 | Green | 340/5 MP |
| 4,058,001 | 11/1977 | Waxman | 73/620 |
| 4,059,010 | 11/1977 | Sachs | 128/660 |
| 4,065,976 | 1/1978 | Taenzer et al. | 73/633 |
| 4,143,554 | 3/1979 | Nagy et al. | 73/644 |

*Primary Examiner*—Stephen A. Kreitman
*Attorney, Agent, or Firm*—Watts, Hoffmann, Fisher & Heinke Co.

[57] ABSTRACT

A real time scanned transducer ultrasonic imaging system is disclosed having an improved mechanical scanning system for reciprocating its transducer. The transducer is immersed in a fluid containing chamber. The drive system includes monitoring equipment which produces signals indicating transducer position. Imaging electronics processes (1) electrical signals produced by the transducer in response to ultrasonic echoes, and (2) the transducer position signals from the monitor. Display apparatus produces substantially real time ultrasonically derived images. The drive system includes a transducer carriage which reciprocates on guide rod structure. A drive arm is coupled to the carriage by a compliant coupling element. A drive shaft attached to the drive arm extends through a wall of the chamber, such that the drive shaft oscillates the drive arm.

14 Claims, 7 Drawing Figures

TRANSDUCER DRIVE FOR ULTRASONIC IMAGING

BACKGROUND OF THE INVENTION

1. Field of the Invention

This invention pertains to the field of ultrasonic imaging for medical diagnostic purposes. Systems for such diagnostic imaging include an ultrasonic transducer, imaging electronics, and display apparatus. The imaging electronics actuate the transducer for propagating incident ultrasonic energy into a patient's body. Within the patient's body, the ultrasonic energy causes echoes at interfaces between body tissues having differing acoustical impedance characteristics. Some of these echoes are reflected back to the transducer, which converts them to electrical output signals. The imaging electronics process the electrical output signals to cause the display apparatus to produce visual images representing structure of the patient.

One ultrasound system is known as a real time B scanner whose transducer is located in a chamber or vessel containing a water bath. Drive apparatus moves the transducer along a path within the water bath, simultaneously with the production of bursts of ultrasonic energy by the transducer. The drive system includes monitoring equipment which produces signals indicating transducer positions along the path.

In use, an operator positions the water bath chamber over a region of interest of a patient. The drive apparatus moves the transducer and the imaging electronics initiate the ultrasonic energy production. The electrical signals processed by the transducer in response to the echoes from these incident pulses, and the transducer position indicating signals, are processed to produce a rapid series of visual images of the patient. Such images are typically produced at a rate of approximately 15 to 30 per second, enabling the visualization of motion of, or changes in, internal components and organs of the subject's body.

A discussion of various ultrasonic techniques, including the known B scan method, is found in an article entitled "Methods of Acoustic Visualization", by Green, P. S. et al, *International Journal of Nondestructive Testing*, Vol. I (1969) pp. 1-27. Another example of such a system is described in United States patent application Ser. No. 725,178, filed Sept. 21, 1976, now U.S. Pat. No. 4,141,347, by Green, et al entitled REAL TIME ULTRASONIC B-SCAN IMAGING AND DOPPLER PROFILE DISPLAY SYSTEM AND METHOD.

2. Description of the Prior Art

Mechanical drive systems are known for moving transducers in the described real time B scan systems. U.S. Pat. No. 4,065,976 issued Jan. 3, 1978 to Taenzer, et al discloses one proposed system which has been used clinically in a research atmosphere but which has not been made commercially. With this proposal, transducer mounting structure forming an articulated parallelogram is used. The parallelogram structure includes two relatively long side legs, and two relatively shorter end legs which are pivotally connected together. An ultrasonic transducer is mounted on one of the shorter legs. The transducer and the articulated parallelogram structure are immersed for motion in the water bath.

The end leg of the parallelogram structure opposite the transducer is supported within the water bath. In operation, drive structure, powered by an electric motor, and coupled to the parallelogram structure, articulates the structure. This motion causes the transducer to move along a curved path. During motion, the transducer is actuated by electrical signals transmitted over leads extending from the imaging electronics outside the water bath and through the walls of the fluid bath chamber.

While the drive system described above has exhibited utility it has several attendant disadvantages. These disadvantages stem from (1) the size, mass and complexity of the system; (2) the excessive agitation of the bath during system operation; (3) mechanical balancing problems; (4) water sealing difficulties associated with multiple members extending through the fluid chamber walls, (5) nonlinearity of the relation between the transducer position and the drive structure operation, and (6) the large number of moving parts which result in unneeded complexity and cost.

Another problem with a parallelogram system is that its multiplicity of parts all exhibit hydrodynamic drag when rapidly moved in water. This phenomenon produces stresses upon the moving parts and their connecting structures, and requires considerable power to maintain their movement at the rapid speeds desired, and with the required precision for imaging. The additional power requirement further increases the size, weight and complexity, as well as the cost, of the drive system.

The motion of all these parts also undesirably agitates the water bath. Moreover, the fact that the curved transducer motion path has components extending in more than one direction complicates this problem. As a result of water agitation images may be blurred and the life expectancy of components, such as bearings, is unduly limited.

In addition, the parallelogram system is inherently difficult to balance mechanically, and this difficulty in balancing leads to the presence of undue vibration in the scanner unit when in operation. The vibration problem is aggravated by the relatively high moving mass of the system.

Another drawback of this prior system is that it requires multiple elements penetrating the walls of the water bath chamber. Each penetration requires an associated sealing structure, which increases the cost and complexity of the system. Moreover, the seals, particularly those associated with movable parts, tend to fail after extensive use.

SUMMARY OF THE INVENTION

This invention provides an improved transducer drive system for a real time ultrasonic scanning imaging system which obviates or reduces the diadvantages described above and provides certain advantages as well.

Generally, the novel drive system includes structure mounting the transducer for reciprocal motion along a path, and a drive member supported for oscillatory movement. A compliant coupling element extends between the drive member and the transducer to convert rotative movement of the drive member into reciprocal motion.

In accordance with a more specific aspect of the invention, the transducer mounting structure includes a movable carriage for supporting the transducer. An elongated guide structure supports the carriage and transducer for reciprocal, rectilinear motion.

In accordance with this aspect, rotative motion of a single drive member is easily accomodated to effect reciprocal transducer motion. The motion of the transducer is accomplished without the need for a large number of articulated transducer coupling elements assembled in a complex fashion.

This structure provides a drive system which is simpler, less massive, smaller in size and less costly than previous systems. The system requires less power to operate, and causes less agitation or "pumping" of the fluid bath than previous systems.

A still further advantage of this invention is that, for drive member rotation below about 35 degrees, there is a practically linear transfer function between drive shaft angular position and transducer position. This linear transfer function facilitates monitoring of transducer location by the use of common and simple devices, such as potentiometers and shaft encoders, which themselves have linear transfer functions and are thus compatible with the mechanics of the present system.

In accordance with another feature of the invention, the mechanical drive system includes a drive arm coupled to the transducer and mounted for oscillatory motion, and a drive shaft rotatably fixed with respect to the drive arm for oscillating the drive arm in response to power applied to the drive shaft. The drive shaft and drive arm cooperatively define a conduit internal to the shaft and arm and extending longitudinally with respect to them. The conduit leads from the proximity of the transducer to a location external to the system. The system further comprises electrical connecting means, such as a coaxial cable, disposed in the conduit and coupled electrically to the transducer.

This arrangement, with its internal conduit, facilitates electrical connection of the transducer to external circuitry by way of the interior of the drive arm and shaft. An advantage of this feature is that, where the drive arm and transducer are immersed in a water bath chamber, as is normal, electrical leads being within the internal portions of the shaft and arm eliminates need for a separate liquid seal for an electrical connector passing from the transducer out of the water bath chamber. Rather, the connector exits the water bath through the interior of the drive shaft. The drive arm and shaft combination has its own external sealing where it penetrates a wall of the chamber, and this same seal is used to accommodate the electrical leads as well.

In accordance with a more specific aspect of this feature, an ultrasonic transducer scanner assembly includes structure defining a chamber for containing the fluid bath and an electroacoustical transducer within the bath. The assembly further includes a substantially elongate mechanical drive structure coupled to the transducer and having a portion thereof extending through a wall of the chamber for reciprocally moving the transducer in response to the application of power to the drive structure. The drive structure defines an elongate conduit extending through the portion of the drive structure which traverses the wall of the vessel, and an electrical connecting means extends through the conduit from outside the chamber to the region of the ultrasonic transducer.

In accordance with a more specific feature of this invention, the compliant coupling member between the drive member and the transducer comprises a portion of electrically conductive material for facilitating connection between the ultrasonic transducer and electrical leads extending through the internal conduit defined by the drive member.

The system of this invention also incorporates specific mechanical balancing features for minimizing vibration of the transducer assembly. In accordance with this aspect, the inventive system includes a drive arm mechanically coupled to the transducer. A pivotally supported drive shaft is coupled to the drive arm for effecting rotative movement of the drive arm in response to the rotation of the drive shaft. Balance weighting structure is fastened to the drive shaft for positioning the net center of mass of the movable system components at or near the shaft axis. A further balancing element is rotatably mounted on the drive shaft. Cranking structure responsive to the application of power is provided for oscillating the drive shaft. The cranking structure is also mechanically coupled to the balance element for oscillating the balance element with respect to the drive shaft, but out of phase with the motion of the drive shaft.

The provision of the balance weighting structure, rotationally fixed to the drive shaft, balances the moments of inertia of the mechanical drive system about its pivot point. This counteracts the tendency toward the creation of transverse forces at the pivot point in response to rapid oscillation of the drive shaft. The balance member which is rotatable with respect to the drive shaft is provided so that its connection to the cranking structure for rotation out of phase with the drive shaft counteracts the effect of tortional moments of inertia, as generated by the power input to the cranking structure.

This invention will be understood in more detail by reference to the following detailed description, and to the drawings, in which:

DESCRIPTION OF THE PREFERRED EMBODIMENT

Figure 1:
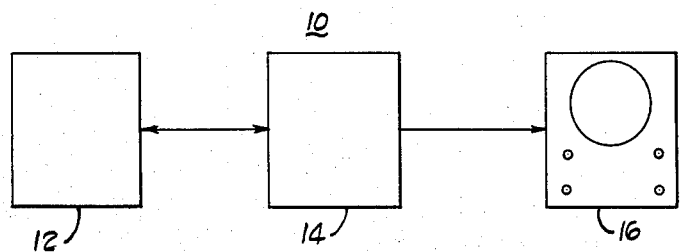
FIG. 1 is a block diagram illustrating an ultrasonic imaging system incorporating the present invention.

A real time mechanically scanned ultrasonic imaging system 10 is shown in block form in FIG. 1. The system 10 propagates bursts of incident ultrasonic energy into a subject, such as a human patient, and produces real time images of the patient by the use of electrical signals representing ultrasonic echoes.

The system 10 includes a transducer scanning unit 12, imaging electronics 14 and display apparatus 16. The transducer unit 12 includes structure defining a chamber for containing a liquid bath in which an ultrasonic transducer is immersed. The unit 12 also includes mechanical scanning drive apparatus for reciprocally scanning the transducer along a predetermined rectilinear path. The unit 12 also includes monitoring apparatus for producing electrical signals indicating the instantaneous position of the transducer along its path.

The imaging electronics includes power circuitry for actuating the ultrasonic transducer to propagate bursts of ultrasonic energy as the transducer is scanned along its path. The transducer produces electrical output signals representing ultrasonic echoes which are produced at interfaces between body tissue having differing characteristics. These echo-representing electrical signals are directed to the imaging electronics 14, as are the signals representing transducer location.

The imaging electronics 14 processes the echo-representing signals and the position representing monitor signals. The display apparatus utilizes the processed signals to produce a rapid succession of substantially real time ultrasonically derived images which describe the internal structure or condition of the patient's body in the region studied.

The imaging electronics 14 and display apparatus 16, as well as the ultrasonic transducer, can suitably be provided in accordance with information in the referenced article and patent.

Figure 2:
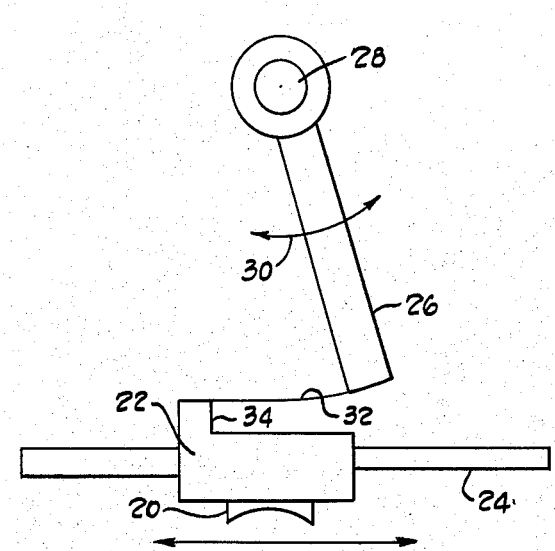
FIG. 2 is a diagrammatic drawing illustrating a portion of the system shown in FIG. 1.

FIG. 2 shows a portion of the transducer drive of the present system. An ultrasonic transducer 20 is mounted on a carriage member 22. The transducer 20 is a suitable piezoelectric device which responds to electrical signals to produce acoustical energy, and which responds to the receipt of acoustical energy to produce corresponding electric signals.

The carriage 22 is mounted for reciprocal motion upon a linear guide rail 24. A drive arm 26 is fixed to a drive shaft 28, and both the drive arm and drive shaft are supported for rotative motion about the drive shaft axis. In response to the application of reciprocating rotative force to the drive shaft 28, the drive arm 26 is caused to oscillate back and forth about the drive shaft axis in the directions indicated by the arrows 30.

The drive arm 26 is coupled to the carriage 22 by means of a compliant coupling element 32 in the form of a leaf spring. The leaf spring 32 is fastened between a protrusion 34 of the carriage 32 and to the lower end of the drive arm 26. Rotation of the drive shaft 28 causes corresponding rotative movement of the drive arm. This movement is employed, by means of the compliant coupling element 32, to move the carriage 22 and its associated transducer 20 back and forth along the guide rail 24 reciprocally.

Thus, a single rotative drive arm is enabled to effect rectilinear movement of the transducer, because of the use of the compliant coupling member. This is significant in part because the drive arm, transducer carriage, transducer and guide rails are all, in operation, immersed in a water bath. The use of a single drive element, and the use of linear motion of the transducer minimizes agitation of the water bath and hydrodynamic drag. The low moving mass attendant on the use of relatively few moving parts also facilitates this rapid scanning, at a rate of approximately 15 cycles per second, and minimizes required power.

The scanning system of this invention provides for a substantially linear transfer function between the angular position of the drive shaft 28 and the position of the transducer 20 on its linear path. This is desirable because most of the monitoring devices available for converting shaft angles to electrical signals, such as potentiometers and shaft angle encoders, have linear transfer functions.

Figure 3:
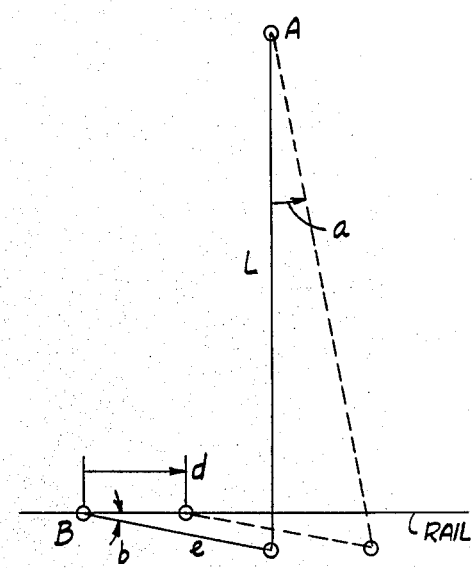
FIG. 3 is a graphical illustration describing geometrical relationships between motion of components of the system illustrated in FIG. 2.

FIG. 3 shows a simplified geometrical model of the mechanical system of this invention and illustrates the relationship between transducer position, d, and drive shaft angle, a. In FIG. 3, the drive shaft 28 is located at A and the carriage is connected at B. The drive arm is rigidly connected to the drive shaft and has a length L. For simplicity, the leaf spring constituting the compliant coupling element is considered to be a pivotally connected link of length l. This approximation is quite adequate because the mechanism is used only over a small range of drive shaft angles. The geometry allows for an initial angle, b, between the leaf spring and the carriage guide rail. When the drive shaft is rotated and the drive arm swings through an angle a, the carriage moves a distance, d, so that the mechanism component positions change from that shown with solid lines to that shown with broken lines. The mathematical relationship between carriage position, d, and shaft angle, a, is:

$$d = l \cos b + L \sin a - l \cos[\sin^{-1} (\sin b - \frac{L - L \cos a}{l} )]$$

Although this relationship is slightly non-linear, by proper choice of drive arm length, L, leaf spring length, l, and initial angle, b, the relationship can be made to represent a good linear approximation over a limited range to within any desired degree of accuracy. For example, with L=5 centimeters, L=1.3 centimeters and b=3°, the transfer function is within 0.5% of a perfect straight line over a 34° drive shaft angular range corresponding to a carriage travel of 3 centimeters. It can be seen that the required dimensions for achieving substantial linearity are quite reasonable. Although the model of FIG. 3 approximates the leaf spring as a pivotally connected link, experiments show excellent agreement between this theoretical basis and the experimentally observed results.

Figure 4:
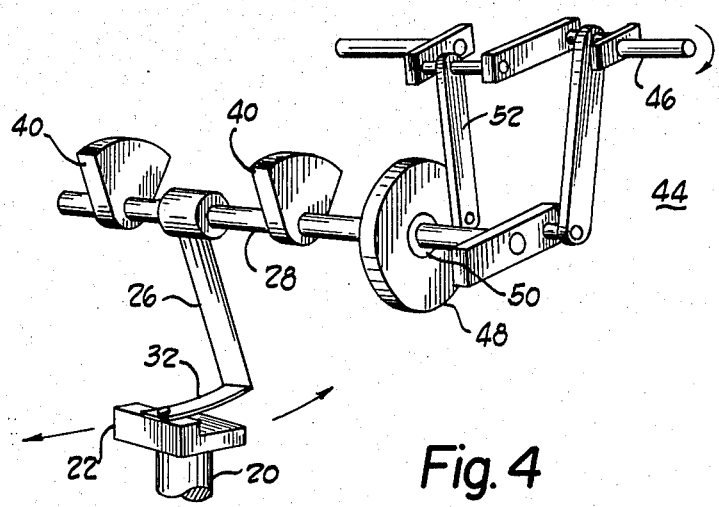
FIG. 4 is a detailed diagrammatic view showing a portion of the system of FIG. 1.

Special novel means are used to enhance the mechanical balance of the drive assembly of this system, minimizing undesirable vibration of the transducer unit 12 of which the drive system is a part. FIG. 4 illustrates in simplified form the technique used for achieving this mechanical balance.

When the drive arm 26 is oscillated back and forth by rapidly reversing rotation of the drive shaft 28, two main sources of vibration are apparent. First, when the drive arm 26 is rotated, transverse forces, oscillating in synchronism with drive arm rotation, appear laterally on the pivot of the drive shaft 28. This manifestation of imbalance is caused by the fact that the center of mass of the movable parts of the drive system is considerably displaced from the axis of the shaft 28, and in fact resides within or near the drive arm 26 between the shaft 28 and the coupling element 32.

To correct for this imbalance, weighting elements 40 are attached to the drive shaft 28. The weighting elements 40 are fixed with respect to the shaft 28, and their mass and location is chosen such that the center of mass of the shaft 28, transducer and carriage 20, 22, drive arm 26 and weighting elements 40 resides proximate the axis of the shaft 28. This feature balances the moments of inertia of the movable components of the drive assembly so that transverse forces on the shaft 28 are counteracted, along with the attendant vibration which would otherwise be caused.

A cranking apparatus, generally indicated at 44, is employed to rotate the drive shaft 28, in response to continuous torque applied to a crank shaft 46. The addition of the weighting members 40 adds to the moment of inertia about the drive shaft 28. Accordingly, these moments of inertia are seen by cranking means driving the drive shaft 28 as irregularities in the amount of power required. Thus, when the drive shaft 28, with its associated movable components, is oscillated at a rapid rate, eg, 15 cycles per second, considerable power is necessary to overcome the rotative inertia of the system to effect the angular acceleration and deceleration required for rapid and precise transducer movement, and this tortional imbalance causes a rotational vibration of the system.

Means for counteracting the moments of inertia of the system's movable components, as seen by the cranking apparatus 44, is provided in the form of a free wheeling balance wheel member 48. The balance wheel member is axially fixed with respect to the drive shaft 28, but is rotatively movable thereon by virtue of the provision of bearing structure 50. The balance wheel 48 is coupled to the cranking apparatus by a lever 52. The cranking apparatus and the lever 52 cooperate to rotate the balance wheel 48 at a frequency equal to that of the reversing rotation of the drive shaft 28. The cranking apparatus 44 and lever 52 cooperate to effect the rotation of the balance wheel 180° out of phase with the rotation of the drive shaft 28.

The balance wheel 48 is constructed such that its moments of inertia about the drive shaft 28 equal the moments of inertia of the shaft 28, weighting elements 40, drive arm 26, carriage 22 and transducer 20. When this constraint is met, the moments of inertia of the balance wheel 48 exactly counteract the moments of inertia of the remainder of the components of the system movable about the shaft 28. This counteraction removes the rotational vibration of the system making its operation smooth and vibration free.

Figure 5:
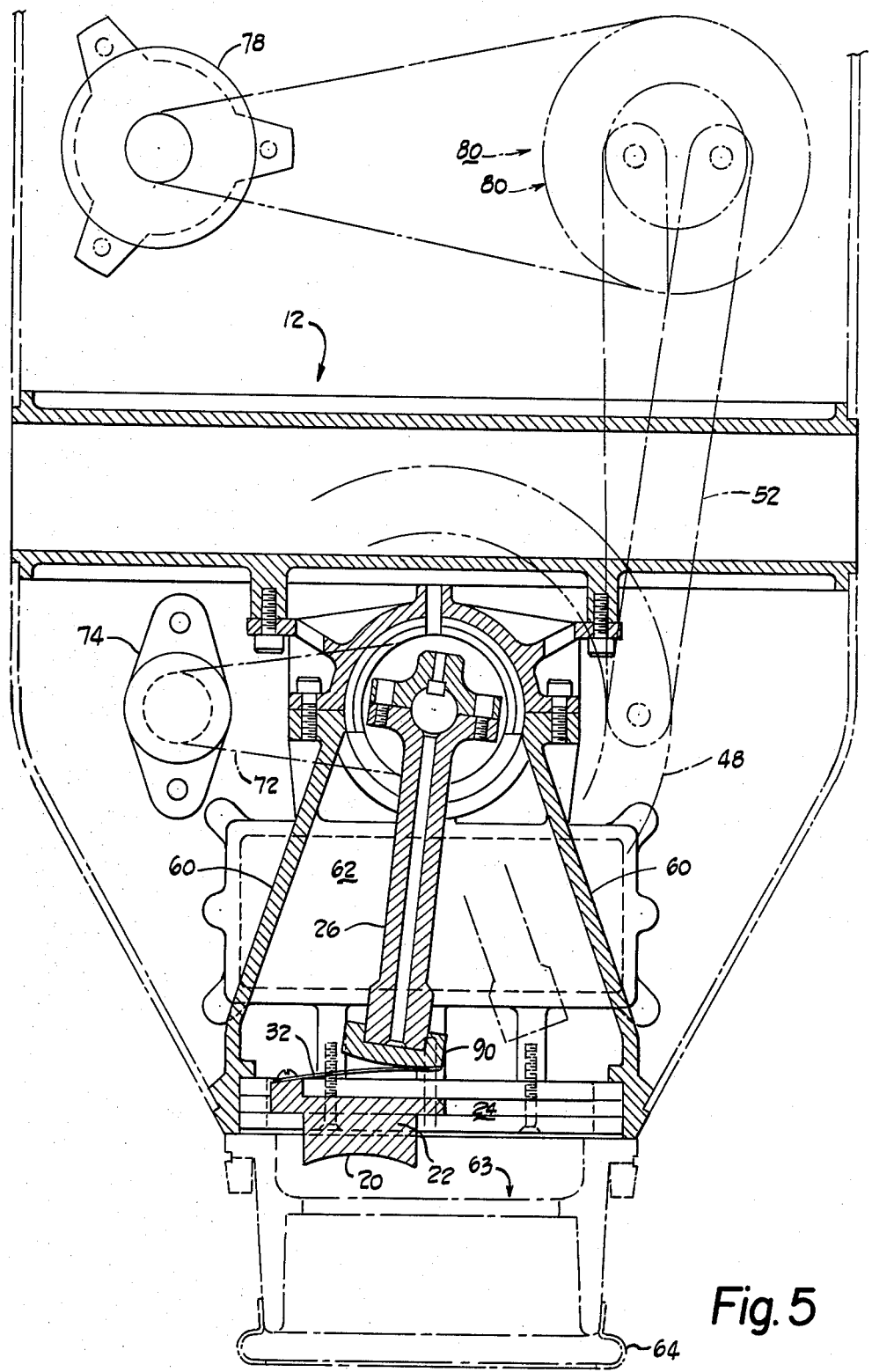
FIG. 5 is a detailed drawing, partially in cross section, showing an elevational view of a portion of the system of FIG. 1.
Figure 6:
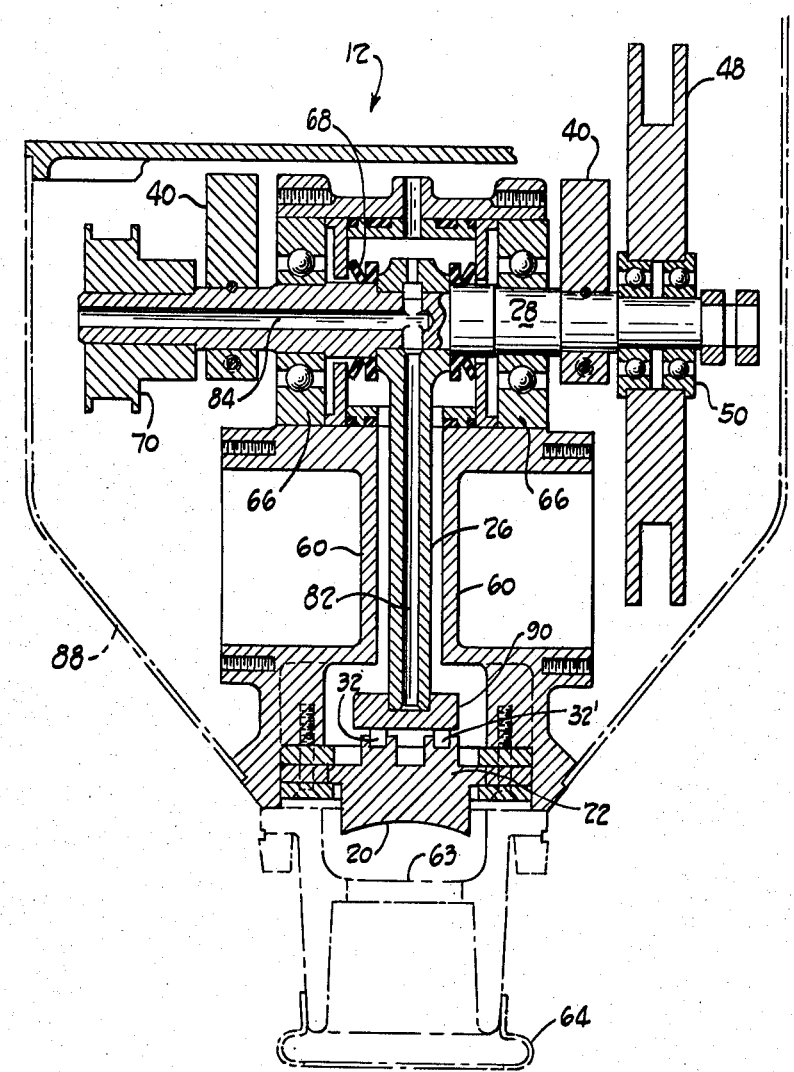
FIG. 6 is a detailed elevational view, partially in cross section, further illustrating the portion shown in FIG. 5.

A transducer unit 12 constructed in accordance with the present invention is shown in detail in FIGS. 5 and 6. FIGS. 5 and 6 illustrate the mounting of the drive arm 26 on the drive shaft 28. The drive arm and drive shaft are enclosed within walls 60 defining a fluid tight chamber 62. The fluid tight chamber 62 communicates with a compliant coupling bag 64 which forms another boundary of the chamber 62. In operation, the coupling bag is used to contact the patient's skin in a region of interest, in order to form an efficient fluid coupling between the transducer and the patient's body.

The drive shaft 28 is mounted for rotation about its axis on bearing structure 66. The drive shaft 28 traverses the walls 60 of the fluid tight chamber 62 in the region of sealing structure indicated at 68. A pulley 70 is located at the left end of the drive shaft 28, as viewed in FIG. 6. Suitable belt means 72 couples the pulley 70 to transducer monitoring apparatus 74. The transducer monitoring apparatus may be a potentiometer or a shaft angle encoder, for example, which converts angular position to an electrical voltage which is a linear function of the angular position. By way of the coupling structure 72, the monitoring apparatus senses the rotational position of the drive shaft 28 and the drive arm 26, and produces an electrical signal which represents the shaft angle. This electrical signal is transmitted by conductive leads (not shown) to the imaging electronics, which processes these signals in the course of generating ultrasonically derived images.

Since the angular position of the shaft 28 is practically a linear function of the transducer position, as explained above, the signal produced by the monitoring apparatus 74 is in turn substantially a linear representation of the transducer position.

The balance weighting elements 40 can be seen in FIG. 6 as offset eccentric members which are rotationally fixed to the shaft 28. The balance wheel 48 and its associated bearing structure 50 is also illustrated in FIG. 6, as being driven by the lever 52, associated with the cranking apparatus 44, which in turn is driven by a suitable electric motor 78. The electric motor 78, by way of the mechanism generally indicated at 80, also drives the shaft 28 out of phase with the rotation of the balance wheel 48. This additional structure, being straightforward and easily provided by those of ordinary skill, for purposes of simplicity is not illustrated in more detail in the drawings.

Novel structure is provided for coupling the electro-acoustical transducer 20 to the imaging electronics 14. FIG. 6 illustrates a portion of this structure. The drive arm 26 defines a longitudinally extending axial internal conduit 82. The conduit 82 communicates with radial conduit 84 defined by the drive shaft 28. The conduit 84 extends from the conduit 82 outwardly through the drive shaft 28, traversing the wall of the chamber 62 within the shaft 28.

In the preferred embodiment, an electrical co-axial cable (not shown in FIG. 6) is disposed in the conduits 82, 84. One end of the co-axial cable is coupled appropriately to the imaging electronics 14. The other end of the co-axial cable within the conduit 82, extends downwardly as in FIG. 6 through the arm 26 to the general region proximate the transducer 20. Thus, a passageway is provided for the electrical leads necessary to connect the transducer to the imaging electronics, without the need for a separate seal through a wall 60 of the chamber 62.

The transducer unit 12 is enclosed within a housing 88, having walls made of a suitably rigid material such as steel, plastic, fiberglass or the like.

Figure 7:
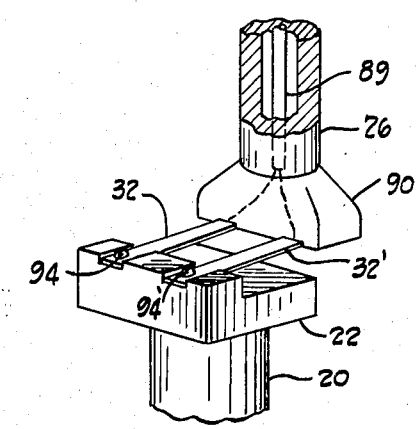
FIG. 7 is a detailed graphical view of a portion of the system as illustrated in FIG. 4.

FIG. 7 shows structure for connecting the transducer 20 to the end of the electrical co-axial cable. The drive arm 26 is partially broken away, revealing electrical co-axial cable 89 extending therethrough. The two conductive parallel portions constituting the co-axial cable 89 separate within an insulating block 90 attached to the lower end of the arm 26, and are connected respectively to each of a pair of leaf springs 32, 32' which comprise compliant connecting elements between the insulating block 90 and the carriage 22.

In addition to being mechanically coupled to the carriage, the leaf springs 32, 32', made of conductive material, such as spring steel, are respectively connected electrically to electrical terminals 94, 94'. The terminals 94, 94' are electrically coupled in known fashion to the transducer 20. Electrical signals passing over the co-axial cable 89 are thus transmitted to the transducer 20 to cause the transducer to emit ultrasonic energy. Electrical signals produced by the transducer 20 in response to acoustical energy impinging upon the transducer are transmitted to the co-axial cable, which in turn transmits these signals to imaging electronics by way of the conduits 82, 84.

It will be understood that the embodiment of this invention as described here is intended as illustrative, rather than exhaustive, of the invention. Persons of ordinary skill may be able to make certain modifications, additions to, or deletions from the disclosed embodiment while remaining within the spirit of the invention and its scope, as defined by the appended claims.

What is claimed is:

1. A transducer drive system for a real time scanned ultrasonic imaging system, the drive system comprising:
   (a) structure for mounting the transducer for substantially linear, reciprocal motion along a path;
   (b) a drive member supported for oscillatory movement; and
   (c) a compliant element coupling between the drive member and the transducer.

2. The drive system of claim 1, wherein said mounting structure comprises:
   (a) a movable carriage for supporting the transducer; and
   (b) elongated guide structure engageable with the carriage for supporting the carriage for substantially linear reciprocal motion along the path.

3. The system of claim 1, comprising:
   (a) an electrical terminal for coupling the transducer to electrical circuitry;
   (b) said drive member defining a conduit therein for accomodating at least a portion of the length of an electrical conductor extending through the drive member and between a region proximate said terminal and a region external to the drive system;
   (c) an electrical conductor extending through said conduit; and
   (d) said complaint coupling element comprising an electrical conductor coupled between said electrical conductor and said terminal.

4. The system of claim 1, further comprising:
   (a) a vessel containing a liquid bath in which said transducer, mounting structure and drive member are immersed; and
   (b) supporting structure comprising a drive shaft extending through a wall of said vessel and rotatably fixed with respect to said drive member for affording means for oscillating said drive member by the application of power to said drive shaft.

5. The system of claim 4, further comprising:
   (a) said drive member comprising an elongated arm;
   (b) pivot structure extending through said wall; and
   (c) said drive shaft extending through said wall and pivot structure for engaging the drive arm.

6. The system of claim 5, wherein:
   (a) said drive arm defines a first longitudinal conduit therein and extending to a region proximate the transducer;
   (b) said drive shaft defines a second conduit therein communicating in series with the first conduit; and
   (c) said system further comprises an electrical conductor extending through said conduits between the region of the transducer and the exterior of the liquid containing vessel.

7. A mechanical drive system for reciprocally scanning an electro-acoustic transducer in an ultrasonic imaging system, said mechanical drive system comprising:
   (a) a drive member coupled to the transducer and mounted for reciprocal motion;
   (b) a second drive member fixed with respect to the drive arm for reciprocally moving the drive member in response to power applied to the second drive member;
   (c) said second drive member and drive member cooperatively defining a conduit internal to said drive members and longitudinal with respect thereto, leading from the proximity of the transducer to a location external to the system; and
   (d) electrical connecting means disposed in said conduit and coupled electrically to said transducer for facilitating electrical coupling of the transducer to external circuitry.

8. A mechanical system for reciprocally moving an ultrasonic transducer for a real time mechanically scanned ultrasonic examination system, said drive structure comprising:
   (a) a pivotally supported drive arm mechanically coupled to the transducer;
   (b) a drive shaft coupled to the drive arm for effecting rotative movement of the drive arm in response to rotation of the drive shaft;
   (c) balance weighting structure coupled to said drive shaft, the center of mass of said weighting structure being positioned relative to said drive shaft and drive arm for counteracting transverse forces produced on said drive shaft in response to oscillatory rotation of said drive shaft and said drive arm;
   (d) a balance element rotatably mounted on and with respect to said drive shaft; and
   (e) cranking structure responsive to the application of power thereto for oscillatory rotating said drive shaft, and also being coupled to said balance element for oscillatory rotating said balance element out of phase with the rotation of said drive shaft for counteracting the torsional forces of said drive arm, drive shaft and weighting structure.

9. A mechanical drive system for reciprocating an ultrasonic transducer in an ultrasonic investigation system, said drive system comprising:
   (a) a single pivotally supported drive member for coupling to a transducer;
   (b) means for oscillating the drive member in response to the application of power;
   (c) structure for coupling said drive member to said transducer for effecting substantially linear transducer motion in response to rotation of said single drive member.

10. A support and drive assembly for reciprocating an ultrasonic transducer of an ultrasonic imaging system in which the transducer is immersed in a water bath, said assembly comprising:
    (a) guide structure for supporting said transducer for substantially linear reciprocal motion in said water bath; and
    (b) drive means comprising a single pivotally mounted drive arm coupled between said transducer and the exterior of said water bath for effecting said substantially linear motion in response to the application of power thereto.

11. An ultrasonic imaging system comprising:
    (a) an ultrasonic transducer;
    (b) structure for mounting the ultrasonic transducer for linear reciprocal motion along a path;
    (c) a drive member supported for reciprocal movement;
    (d) a compliant element coupling between the drive member and the transducer;
    (e) monitoring means for producing monitor signals indicating the position of the transducer along the linear path;
    (f) imaging electronics for actuating the transducer to propagate bursts of ultrasonic energy into a subject, and for processing electrical signals from the transducer produced in response to ultrasonic echoes, and for processing the monitor signals indicating transducer position; and (g) display apparatus responsive to the electrical signals and monitor signals to generate a series of substantially real time ultrasonically derived images describing internal structure or condition of the subject.

12. A method for reciprocating an ultrasonic transducer in a real time scanned ultrasonic imaging system, said method comprising the steps of:

(a) guiding the transducer for rectilinear reciprocal motion along a path;

(b) imparting reversing rotative motion to a single drive member; and (c) inducing rectilinear motion in said transducer in response to the rotative motion of said single drive arm.

13. A method for mechanically balancing rotative components of a transducer drive system of a real time mechanically scanned ultrasonic imaging system, the system including a pivotally mounted drive member and a drive shaft rotationally fixed to the drive member for causing reciprocal motion of the drive arm in response to the application of power to the drive shaft, said method comprising the steps of:

(a) providing a balance weighting component rotationally fixed to said drive shaft having a mass and location calculated to place the center of mass of said rotative structure at approximately the axis of said pivot;

(b) providing a free wheeling balance element mounted on, but rotationally movable with respect to, the drive shaft;

(c) reversely rotating the drive shaft by the use of power applying structure; and (d) reversely rotating the free wheeling balance member out of phase with the rotation of the drive shaft by the use of said power applying structure.

14. An ultrasonic imaging system comprising:

(a) structure defining a chamber for containing fluid;

(b) an ultrasonic transducer located within the chamber;

(c) a carriage for supporting the transducer;

(d) an elongated guide rod structure engageable with the carriage for constraining the carriage and transducer for linear motion within the chamber;

(e) a single drive arm within the chamber;

(f) a drive shaft rotationally fixed with respect to the drive arm and extending through an aperture in the chamber;

(g) bearing structure for supporting the drive arm and drive shaft for effecting rotational reversing motion of the drive arm in response to torque applied to the drive shaft;

(h) a pair of compliant conductive leaf spring coupling members extending between the drive arm and the carriage;

(i) balance weighting structure rotationally fixed with respect to the drive shaft for balancing moments of inertia about the bearing pivot structure;

(j) a free wheeling balance wheel member mounted on, but rotationally movable with respect to, said drive shaft;

(k) cranking structure responsive to power input thereto for reversely rotating the drive shaft, and for reversely rotating the balance wheel out of phase with the rotation of the drive shaft;

(l) said drive arm and drive shaft cooperatively defining therein an internal conduit extending generally longitudinally with respect to said arm and shaft from a location proximate said coupling elements to the exterior of the fluid chamber by way of the interior of the drive shaft;

(m) a co-axial electrical cable extending through said conduit from external of the fluid chamber and being coupled to said pair of coupling elements; and (n) said coupling elements being electrically coupled between said electrical co-axial cable and electrical terminals on the transducer.

* * * * *

UNITED STATES PATENT AND TRADEMARK OFFICE
CERTIFICATE OF CORRECTION

PATENT NO. : 4,238,962
DATED : December 16, 1980
INVENTOR(S) : JON C. TAENZER

It is certified that error appears in the above-identified patent and that said Letters Patent are hereby corrected as shown below:

Column 2, line 52, "diadvantages" should be --disadvantages--.
Column 6, line 29, "L", second occurrence, should be --l--;
  and line 40, "mimimizing" should be --minimizing--;

Column 10, lines 25 and 27, "oscillatory" should be --oscillatorily--.

Signed and Sealed this

Ninth Day of June 1981

[SEAL]

Attest:

RENE D. TEGTMEYER

*Attesting Officer*   *Acting Commissioner of Patents and Trademarks*